United States Patent
Domenici et al.

(10) Patent No.: US 9,387,164 B2
(45) Date of Patent: Jul. 12, 2016

(54) METHODS OF TREATING CHRONIC SIMPLE GLAUCOMA WITH OPHTHALMIC PREPARATIONS BASED ON BDNF (BRAIN-DERIVED NEUROTROPHIC FACTOR)

(75) Inventors: Luciano Domenici, Budapest (HU); Luca Giovannini, Budapest (HU); Marco Sanso', Budapest (HU)

(73) Assignee: HMFRA HUNGARY LIMITED LIABILITY COMPANY, Budapest (HU)

( * ) Notice: Subject to any disclaimer, the term of this patent is extended or adjusted under 35 U.S.C. 154(b) by 296 days.

(21) Appl. No.: 13/509,824

(22) PCT Filed: Nov. 12, 2010

(86) PCT No.: PCT/IB2010/003220
§ 371 (c)(1),
(2), (4) Date: Jun. 28, 2012

(87) PCT Pub. No.: WO2011/058449
PCT Pub. Date: May 19, 2011

(65) Prior Publication Data
US 2012/0258916 A1 Oct. 11, 2012

(30) Foreign Application Priority Data
Nov. 16, 2009 (IT) .............................. MI2009A2012

(51) Int. Cl.
*A61K 38/00* (2006.01)
*A61K 38/18* (2006.01)
*C07K 14/475* (2006.01)
*C07K 14/48* (2006.01)
*A61K 9/00* (2006.01)

(52) U.S. Cl.
CPC ............. *A61K 9/0048* (2013.01); *A61K 38/185* (2013.01)

(58) Field of Classification Search
CPC ....... A61K 45/06; A61K 38/00; A61K 31/00;
A61K 47/48215; A61K 47/42; A61K 9/0048;
A61K 2300/00; A61K 38/1709; A61K 9/14;
C07K 14/16; B01F 3/0807; G01N 2800/16;
A01N 1/0226
See application file for complete search history.

(56) References Cited

U.S. PATENT DOCUMENTS 6,056,950 A * 5/2000 Saettone et al. ............ 424/78.04
6,261,545 B1 * 7/2001 Okamoto .................... 424/78.04
7,625,927 B2 * 12/2009 Klimko et al. ................ 514/309

FOREIGN PATENT DOCUMENTS

EP 0 958 831 A 11/1999
WO 2009/044423 A 4/2009

OTHER PUBLICATIONS

JP2003-048851 English version (Masayoshi et al.).*
Database WPI, Week Apr. 4, 2003, Thomson Scientific, London, GB; AN 2003-461699, XP002586588, -& JP 2003 048851 (Nidek Co. Ltd.).
Emilia Ghelardi, et al., "A Mucoadhesive Polymer Extracted from Tamarind Seed Improves the Intraocular Penetration and Efficacy of Rufloxacin in Topical Treatment of Experimental Bacterial Keratitis," Antimicrobial Agents and Chemotherapy, vol. 48, No. 9, Sep. 2004, pp. 3396-3401, XP002586589, ISSN: 0066-4804.
Rolando, M. and Valente, C., "Establishing the Tolerability and Performance of Tamarind Seed Polysaccharide (TSP) in Treating Dry Eye Syndrome: Results of a Clinical Study," BMC Ophthalmology, Biomed Central, London, GB LNKD-DlO:10.1186/1471-2415-7-5, vol. 7, No. 1, Mar. 29, 2007, XP021023229, ISSN: 1471-2415.

* cited by examiner

*Primary Examiner* — Chang-Yu Wang
(74) *Attorney, Agent, or Firm* — Silvia Salvadori, P.C.; Silvia Salvadori

(57) ABSTRACT

The present invention relates to ophthalmic preparations in the form of eyedrops based on BDNF (Brain-Derived Neurotrophic Factor).
Said preparations can be administered topically to the intact eye surface, and are useful in the prevention and treatment of neurodegenerative disorders of the retina, optic nerve, lateral geniculate body and visual cortex, in order to prevent reduction of visual capacity and restore the normal visual function.

8 Claims, 14 Drawing Sheets

Figure 1:
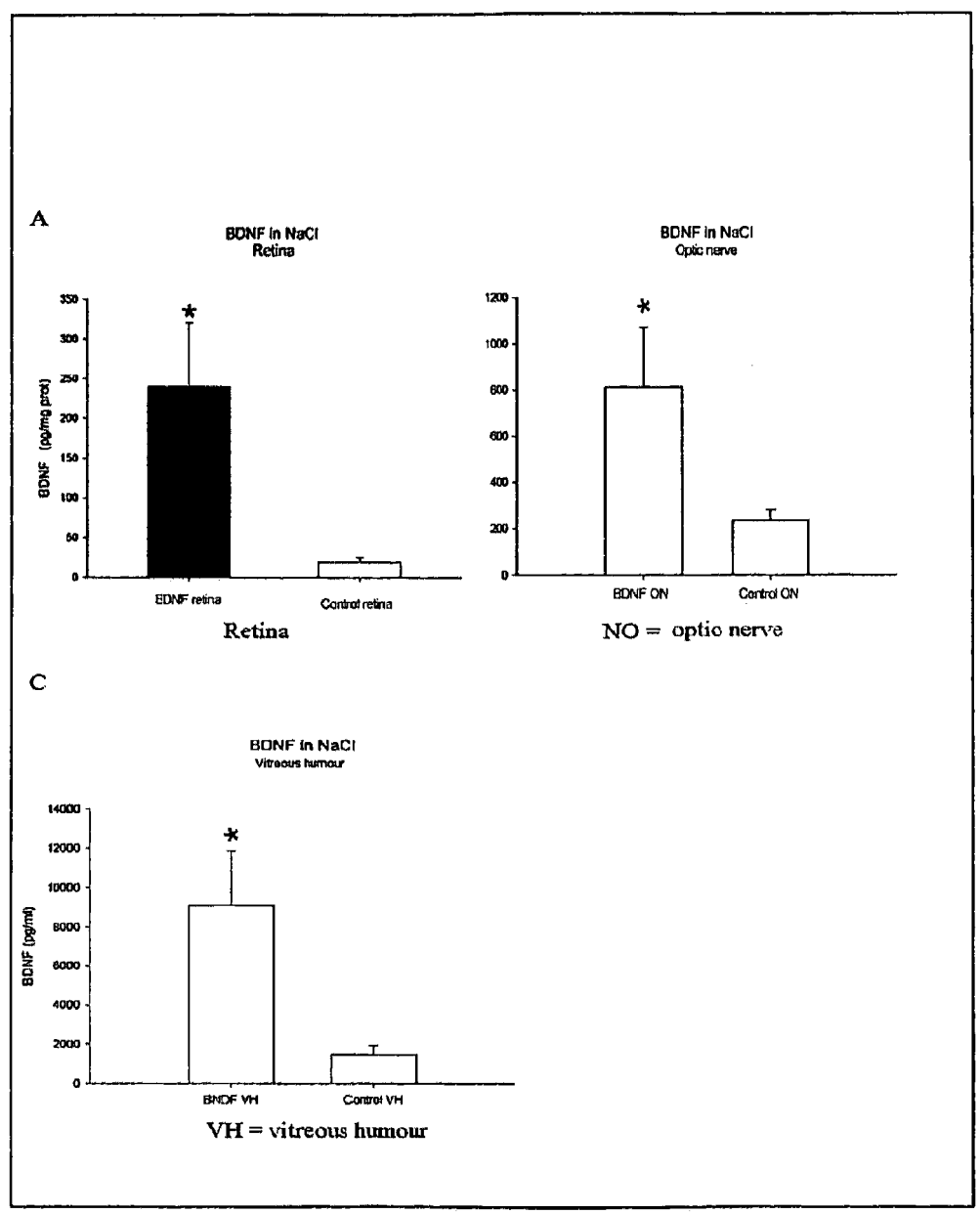

METHODS OF TREATING CHRONIC SIMPLE GLAUCOMA WITH OPHTHALMIC PREPARATIONS BASED ON BDNF (BRAIN-DERIVED NEUROTROPHIC FACTOR)

This application is a U.S. national stage of PCT/IB2010/003220 filed on Nov. 12, 2010 which claims priority to and the benefit of Italian Application No. MI2009A002012 filed on Nov. 16, 2009, the contents of which are incorporated herein by reference.

TECHNICAL FIELD OF INVENTION

The present invention relates to ophthalmic preparations in the form of eyedrops, which contain the brain-derived neurotrophic factor (BDNF) and a viscosity-controlling agent, preferably a galactoxyloglucan extracted from tamarind seeds, also known as TS-polysaccharide or TSP.

Said preparations are useful in the prevention and treatment of neurodegenerative retinal disorders, especially retinitis pigmentosa, glaucoma (including congenital glaucoma, infantile glaucoma, juvenile glaucoma, adult glaucoma, primary open-angle glaucoma, primary angle-closure glaucoma, secondary glaucoma, iatrogenic glaucoma and acute glaucoma), age-related retinopathies such as age-related macular degeneration, vascular and proliferative retinal disorders, detachment of the retina, retinopathy of prematurity (ROP) and diabetic retinopathy, all disorders which lead to blindness.

PRIOR ART

Neurotrophins are proteins synthesised by the nerve cells which control the survival and normal trophism of various cells present in the nervous system.

The best known is nerve growth factor (NGF), discovered by R. Levi-Montalcini and S. Cohen in the mid-20th century.

Other factors, whose protein structure presents structural similarities with that of NGF, were discovered later; consequently, we now consider a class of NGF factors (neurotrophins) to which BDNF, NT-3, NT-4/5 and NT-6 belong as well as NGF (the first three are mainly expressed in the nervous system of mammals, while NT-6 is a new member of neurotrophins identified in teleost fish and absent in mammalian brain).

Neurotrophic factors, including neurotrophins, are released by nerve cells which synthesise them, and bind to specific receptors on the membrane.

Despite their structural similarities, the various neurotrophins act through different receptors, and consequently through different action mechanisms.

Binding of a neurotrophic factor to its specific receptor (TrkA for NGF; TrkB for BDNF, and partly for NT-4; TrkC for NT-3) generates a cascade of events, which elicit a specific response by the nerve cell.

Different neurotrophin receptors are expressed in different areas and, within the same area, in different cells, activating specific intracellular signal transduction pathways. It therefore follows logically that not all areas or nerve cells can respond to each of the four neurotrophins; the limiting factor is the cell distribution of the specific receptor for a given neurotrophin.

The distribution of retinal cells able to synthesise and release NGF, the archetype of the neurotrophins, and the distribution of retinal cells that express the NGF receptor (TrkA), appears very limited, and is restricted in practice to a sub-group of ganglion cells and astrocytic glial cells (Garcia et al., 2003).

EP 1 161 256 B1 describes ophthalmic preparations containing 200 to 500 µg/ml of NGF, to be administered to the intact eye surface for the treatment and/or prophylaxis of disorders affecting the sclera, ciliary bodies, lens, retina, optic nerve, vitreous humour and/or the choroid.

As reported by Lambiase et al., these preparations increase the retinal levels of NGF; however, it can be demonstrated that NGF is unable to perform a neuroprotective effect on the retina.

This agrees with the findings recently reported by Shi et al. (2007). NGF can bind to two types of receptor in the retina, TrkA and P75, which exert opposite effects on the trophism and survival of the nerve cells. When exogenous NGF reaches the retina, it may therefore induce two opposing effects on the retinal cells, which tend to cancel each other out.

Otherwise, BDNF, together with its receptor, TrkB, is abundantly expressed in mammal retina. The retina consists of numerous types of cells arranged in layers. In particular, BDNF is synthesised by some ganglion cells and amacrine cells, such as the dopaminergic cells, present in the inner layer of the retina (Herzog et al., 1994; Perez and Caminos, 1995; Hallbook et al., 1996; Herzog and von Bartheld, 1998; Karlsson and Hallbook, 1998; Bennett et al., 1999; Pollock and Frost, 2003; Seki et al., 2003; Chytrova and Johnson, 2004).

The BDNF receptor, called TrkB, is expressed in numerous types of retinal cells, including ganglion cells, amacrine cells and Müller glial cells (Jelsma et al., 1993; Cellerino and Kohler, 1997; Di Polo et al., 2000).

WO 97/45135 relates to stable pharmaceutical compositions of BDNF in the form of an aqueous solution or lyophilisate. In that document, especially in the section devoted to the prior art, BDNF is mentioned as being useful in the treatment of various disorders, including retinitis pigmentosa. The only form of administration expressly mentioned is injectable preparations.

JP 2003048851 relates to ophthalmic formulations based on BDNF, to be administered in the form of drops on the conjunctiva. The formulations disclosed contain various viscosity-controlling agents, described as being equally effective in carrying BDNF to the retina.

The evidence of activity reported in said document is unconvincing, because the concentration range indicated for BDNF is very wide: 0.001-1 weight/volume %, corresponding to a concentration range of between $1 \times 10^{-2}$ and 10 µg/µl [claim 3, ambit of patent; according to the detailed description of the invention [0006], paragraph 3, but in the example reported, the concentration used is =0.004% (weight/volume %), corresponding to $4 \times 10^{-2}$ µg/µl, ie. much lower than the effective concentrations able to increase the retinal levels of BDNF and prevent the retinal alterations induced by lengthy exposure to light, which are equal to or greater than 15 µg/µl, in the 15-200 µg/µl range, in agreement with the present invention. It should be noted that in JP 2003048851 the application was repeated three times a day (10 µl/application, 0.004% weight/volume) for 5 days, equal to a dose of 1.2 µg/day and a total dose of 6 µg. Even if the daily dose and the total dose are taken into account, they are too low to exert neuroprotective effects; in fact, in agreement with the present invention, a minimum total dose of 150 µg had to be administered topically to obtain neuroprotective effects in the retina subjected to light damage. New data obtained with another experimental model, namely a mouse that develops glaucoma, confirm that of the three BDNF concentrations used (1, 5 and 15 µg/µl), only the highest (15 µg/µl) is effective.

Moreover, JP 2003048851 refers to a retina-protecting effect verified by histological techniques (staining of retina sections with haematoxylin-eosin) designed to measure retinal thickness, but not accompanied by a demonstration of restoration of the retinal function measured by a flash electroretinogram recording, as reported in the present invention. It is well known that in order to demonstrate the neuroprotective efficacy at retinal level of any treatment, results obtained with histological/morphological techniques only are insufficient; evidence of restoration of the retinal functions is also required. It can therefore be concluded that in JP 2003048851, the ophthalmic compositions of BDNF in the concentrations reported in the examples, and more generally in the preferred range, administered externally, are unable to pass from the eye surface to the internal tissue in quantities sufficient to exert a neuroprotective effect able to restore the retinal function.

WO 2006/046584 relates to sustained-release compositions containing HGF, BDNF or PEDF, impregnated with a cross-linked gelatin hydrogel, useful in treating disorders involving lesions of the visual cells, such as retinitis pigmentosa degeneration. In the specific examples, the compositions take the form of microspheres containing doses of BDNF of between 0.001-1000 µg, and can be administered by intraocular injection or subretinal implant.

EP 0 958 831 describes ophthalmic compositions containing a neurotrophic factor selected from a group of factors including BDNF. Said compositions can be applied externally, for example in the form of ophthalmic ointments or solutions, or can be formulated as contact lenses.

The concentration of neurotrophic factor disclosed in EP0958831 ranges from 0.0001 to 0.5% (weight/volume), ie. from $1 \times 10^{-3}$ to 5 µg/l. The concentration ranges reported are therefore very wide. EP0958831 is highly generic, because it relates to various neurotrophic factors, including BDNF, which would be equally effective in the concentration range. It is known that neurotrophic factors are not equally effective in the same concentration range, due to the different densities and distribution of the receptors that determine their biological effects in the different brain areas and individual nerve cells.

Moreover, EP 958831 is extremely vague and unclear about the range of effective BDNF concentrations for topical use: on p. 3 line 44 (see paragraphs 0022 and 0033, claims 19 and 20) two concentration ranges are given, which do not match (range A maximum, between 0.0001 and 0.5% (W/V), equal to a concentration range of between $10^{-3}$ and 5 µg/µl, and range B, between $10^{-3}$ and $2 \times 10^{5}$ µg/l; the two concentration ranges clearly do not correspond. According to the present invention, however, the effective concentrations of BDNF are equal to/greater than 15 µg/µl (range 15-200 µg/µl, ie. higher than range A reported in EP 958831, namely the maximum concentration range. The examples in EP 958831 relate to ophthalmic compositions characterised by a BDNF concentration of 0.02, 0.04 and 10 µg/l, ie. concentrations which are far lower ($1 \times 10^{6}$ times lower) than the lowest concentration which, according to the present invention, has proved effective in raising the BDNF levels in the retina and preventing both light damage and glaucoma damage, namely 15 µg/µl.

It can therefore be concluded that ophthalmic compositions of BDNF at the concentrations reported in EP 958831, administered externally, cannot pass from the eye surface to the internal tissues in quantities sufficient to increase the retinal levels of BDNF, and consequently to perform a therapeutic effect.

NT-4, the other neurotrophin which binds to TrkB, is expressed at a low level in the retina, and only acts on a sub-group of amacrine cells, ie. those which synthesise dopamine (Calamusa et al., 2007).

The absence of BDNF or its receptor causes serious alterations in the retinal function; for example, mice that lack the TrkB receptor (knock-out mice) are characterised by complete loss of the retinal response to light (total absence of b-wave in the flash electroretinogram; Rohrer et al., 1999).

LaVail's group has demonstrated that intraocular injections of BDNF, but not NGF, effectively prevent morphological degeneration of the photoreceptors induced by light damage.

Intraocular injections of BDNF together with other neurotrophic factors have reduced the damage to the retinal ganglion cells which results from lesions of the optic nerve, although it is not yet clear whether BDNF is able to perform neuroprotective effects alone, ie. independently of other neurotrophic factors (Watanabe et al., 2003; Yata et al., 2007).

Other neurotrophic factors such as FGF2 have proved equally effective in preventing morphological alterations caused by light damage, but unlike BDNF, their administration has the undesirable effect of activating factors involved in the inflammatory response (LaVail et al., 1987).

Another neurotrophic factor, CNTF, also prevents morphological degeneration resulting from light damage (LaVail et al., 1978); unfortunately, recent experiments demonstrate that treatment based on CNTF alters the retinal response to light, thus imposing a series of limitations on its potential therapeutic use (McGill et al., 2007).

These results indicate that for neuroprotective purposes in retinal disorder models, it is not sufficient to evaluate the morphological effects of neuroactive molecules; above all, it is essential to assess whether those molecules exert protective effects on the retinal function, and ensure that they do not impair the response of the retinal cells to visual stimuli. There is currently a need to identify new BDNF preparations which can be administered by non-invasive techniques to convey BDNF to the retina, avoiding highly invasive administration techniques such as intraocular, subretinal or retrobulbar injections, which are unsuitable for long-term chronic treatment due to the risk of causing perforation of the eyeball, infections or bleeding, for example.

The present patent proposes topical conjunctival applications in various formulations containing BDNF in a concentration range of between 15 and 200 µg/µl, with a total BDNF dose of between 50 and 4000 µg per administration, according to the size of the eye to be treated, which will depend on the animal species concerned, including humans.

The formulation will preferably contain a viscosity-controlling agent. Said viscosity-controlling agent is preferably a galactoxyloglucan extracted from tamarind seeds (TS-polysaccharide or TSP) having a molecular weight of between 500000 and 800000 Da and the following structural formula:

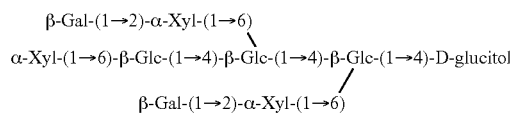

We demonstrate that said preparation, at the concentrations and dose per administration indicated, significantly increases the retinal BDNF levels and prevents i) retinal alterations induced by lengthy exposure to light, and ii) retinal alterations in glaucoma.

It has previously been demonstrated (Uccello-Barretta G et al., 2008; Ghelardi E et al., 2004; Burgalassi S et al., 2000; Ghelardi E et al. 2000) that TSP is able to carry pharmacologically active molecules for topical treatment of the eye surface. By increasing the retention times of the formulation on the eye surface, increased absorption of the active molecules has been observed. This property of TSP has been described in combination with antibiotics (rufloxacin, gentamicin and ofloxacin), antihistamines (ketotifen) and antihypertensives (timolol), all of which are small molecules.

In the case of pharmacological preparations containing recombinant proteins, such as BDNF, the active ingredient is a protein, a molecule with high molecular weight subject to post-translational modifications and adaptation of its spatial bending until it reaches the active three-dimensional configuration. The biological activity of proteins is closely dependent on their three-dimensional configuration, because interactions with the specific receptors and enzymes that recognise them, and consequently, the ability to intervene in the biochemical processes of the target cell, depend on it. The protein configuration can be considerably modified by the environment in which a recombinant protein is to be found. Formulations containing recombinant proteins must therefore ensure that the protein is maintained in solution in its active configuration, and guarantee its stability.

The present invention demonstrates that TSP guarantees the stability of BDNF in the formulation, increases its ocular absorption due to the lengthy residence time of the formulation on the surface, and above all, maintains BDNF in its biologically active configuration.

SUMMARY OF THE INVENTION

It has now been discovered that ophthalmic formulations containing BDNF in concentrations of at least 15 µg/µl prevent retinal alterations induced by lengthy exposure to light, and those associated with increased intraocular pressure in a glaucoma model.

The invention therefore relates to ophthalmic preparations in the form of eyedrops containing brain-derived neurotrophic factor (BDNF). According to a preferred aspect thereof, the compositions to which the invention relates contain galactoxyloglucan extracted from tamarind seeds, known as TSP.

The invention also relates to the use of BDNF to prepare a medicament in the form of eyedrops for the prevention and/or treatment of neurodegenerative disorders of the retina, optic nerve and lateral geniculate body.

The present invention also relates to an ophthalmic preparation in the form of eyedrops containing BDNF for use in the prevention and/or treatment of neurodegenerative disorders of the retina, optic nerve and lateral geniculate body.

LIST OF FIGURES

FIG. 1—Determination of BDNF levels in the retina (A), optic nerve (B) and vitreous humour (C) following topical application of BDNF in saline solution. The BDNF levels are shown on the y-axis, and were measured in the eye treated with BDNF and the control eye treated with saline solution; * indicates the significance of the differences.

Figure 2:
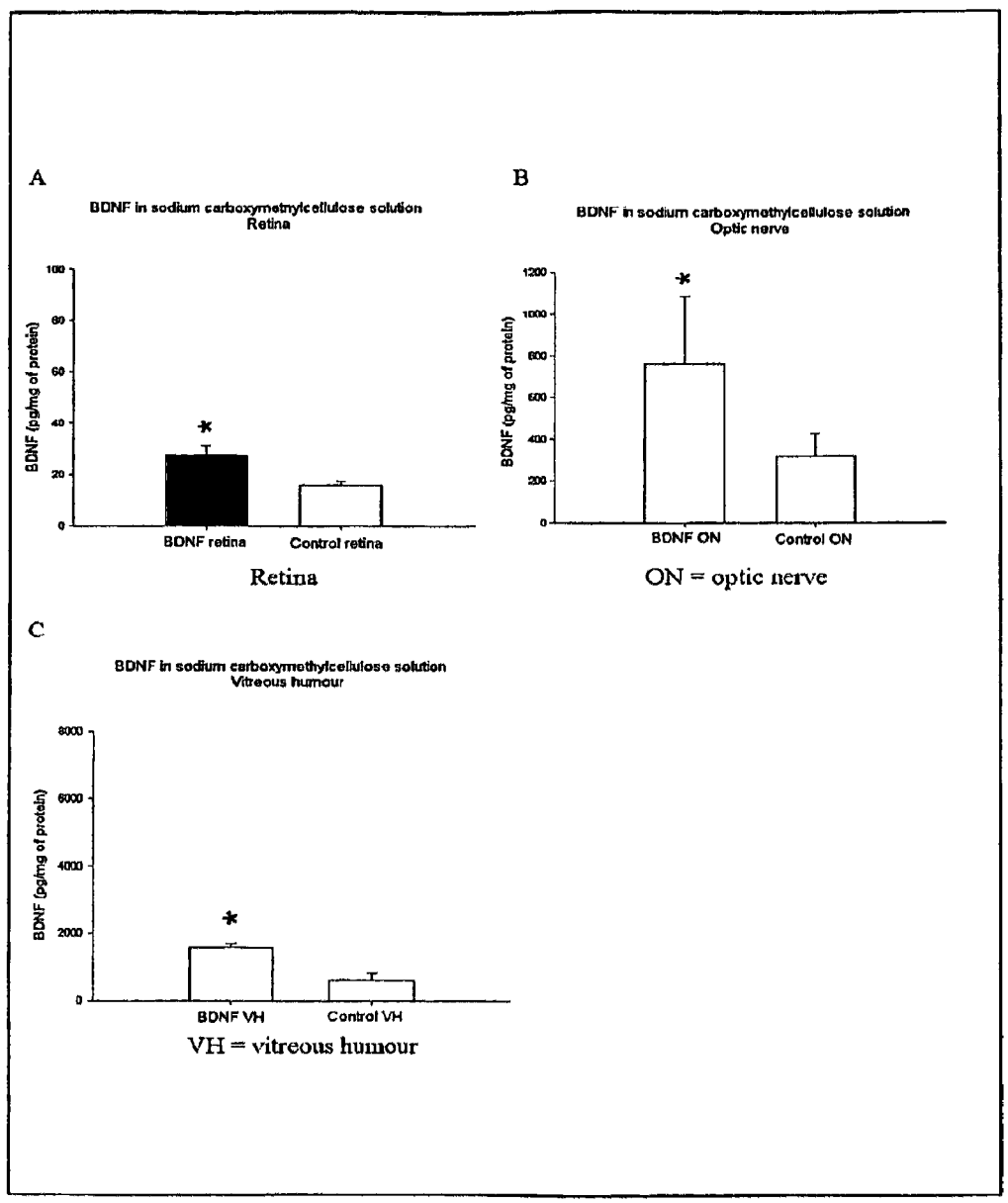

FIG. 2—Determination of BDNF levels in the retina (A), optic nerve (B) and vitreous humour (C) following topical application of BDNF in solution with sodium carboxymethylcellulose. For conventions and symbols, see FIG. 1.

Figure 3:
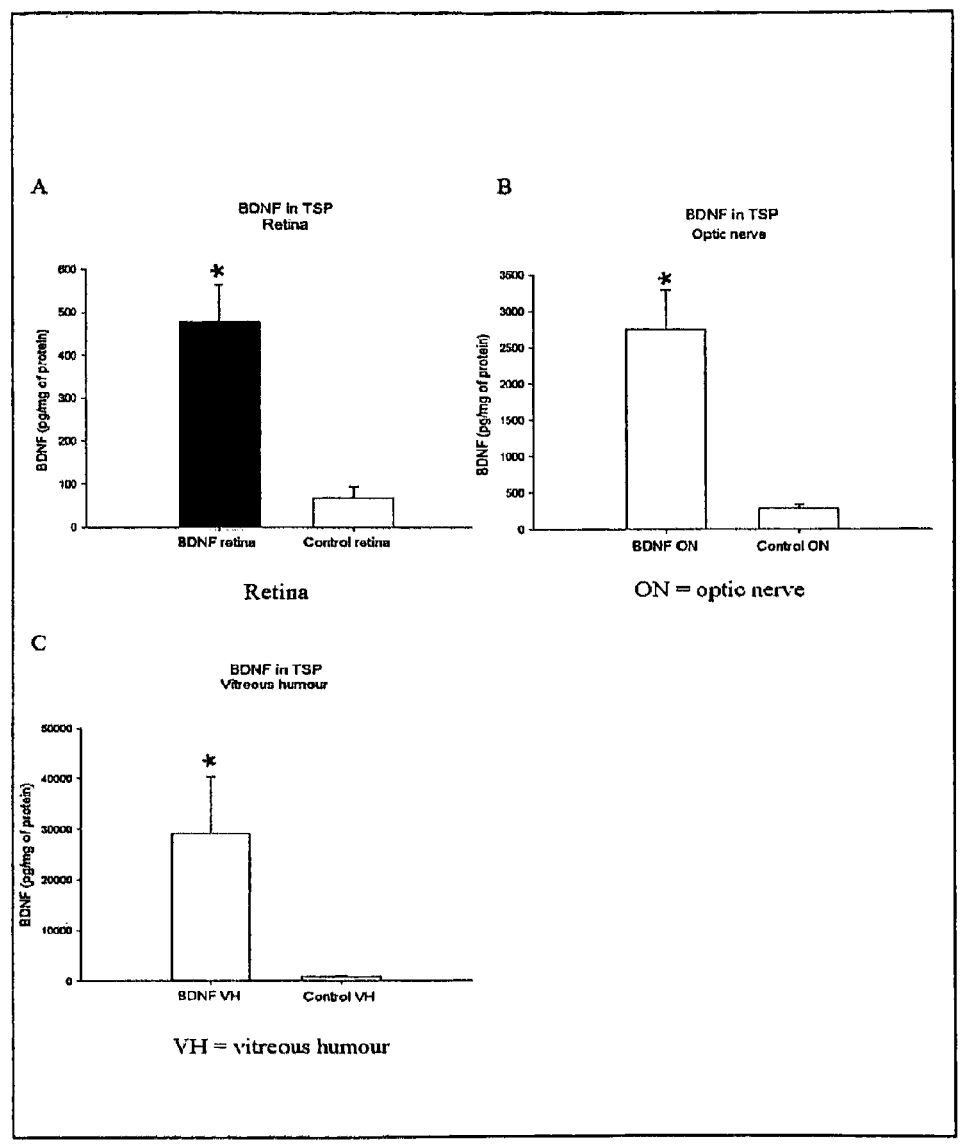

FIG. 3—Determination of BDNF levels in the retina (A), optic nerve (B) and vitreous humour (C) following topical application of BDNF in solution with TSP. For conventions and symbols, see FIG. 1.

Figure 4:
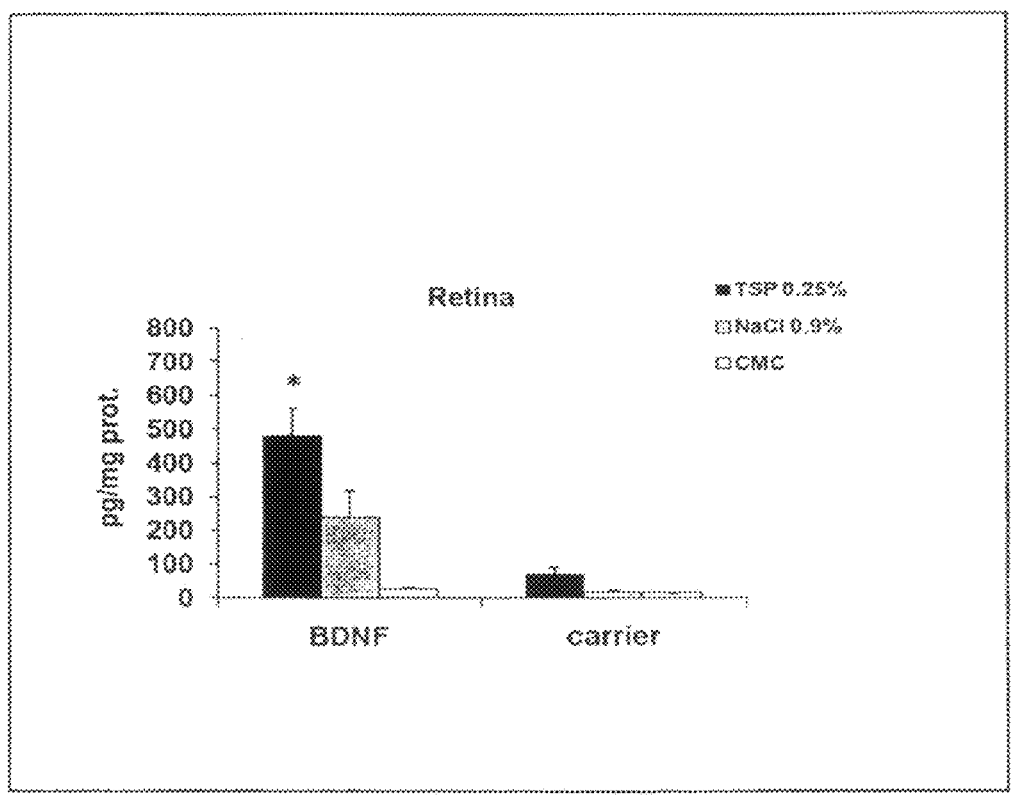

FIG. 4—Comparative efficacy of TSP, saline solution (NaCl) and sodium carboxymethylcellulose (CMC) in carrying BDNF and increasing its retinal concentrations (pg/mg of protein, see x-axis). The retinal levels of BDNF after topical treatment with BDNF in TSP (*) significantly increased, compared with the BDNF level after topical treatment with BDNF in saline solution and sodium carboxymethylcellulose. The data are derived from panel A in FIGS. 1, 2 and 3.

Figure 5:
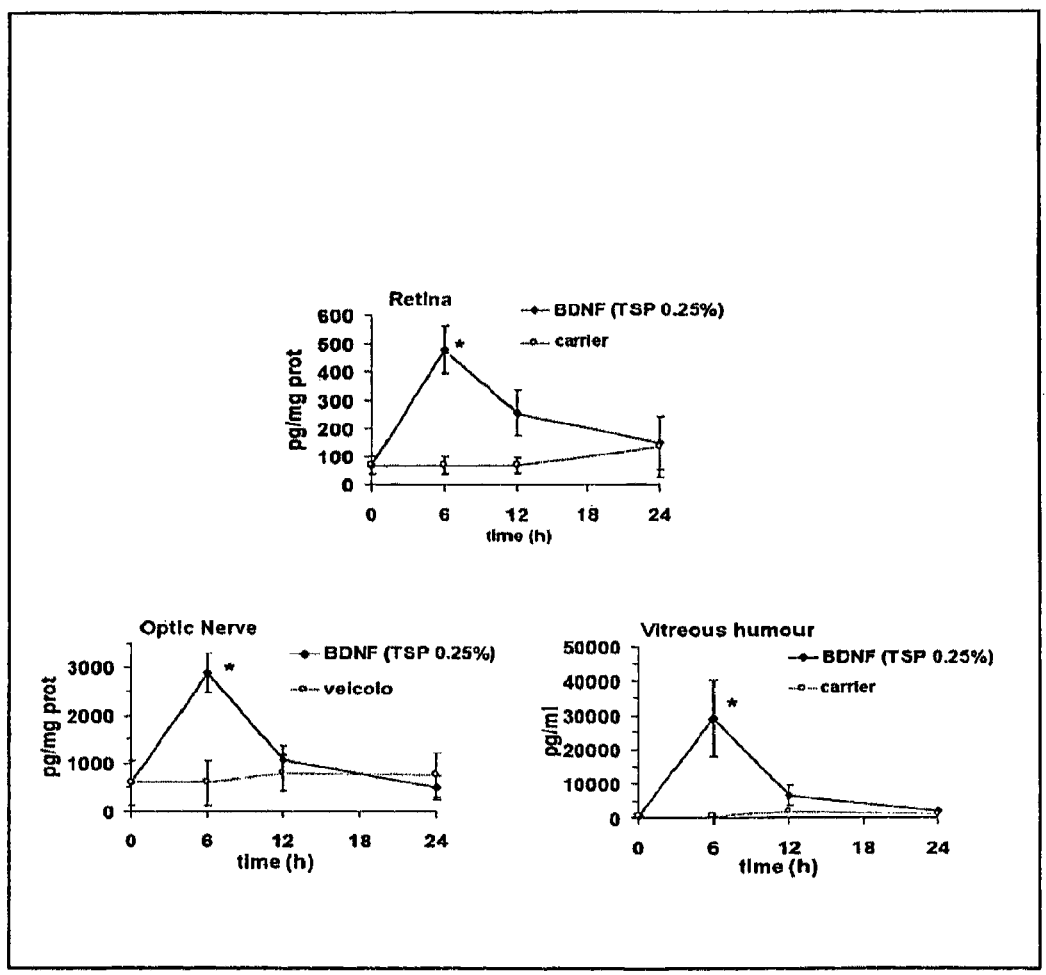

FIG. 5—Kinetics of BDNF levels in the retina, optic nerve and vitreous humour following topical application of BDNF in solution with TSP. The BDNF levels remain significantly high in the first 6 hours after treatment (*).

Figure 6:
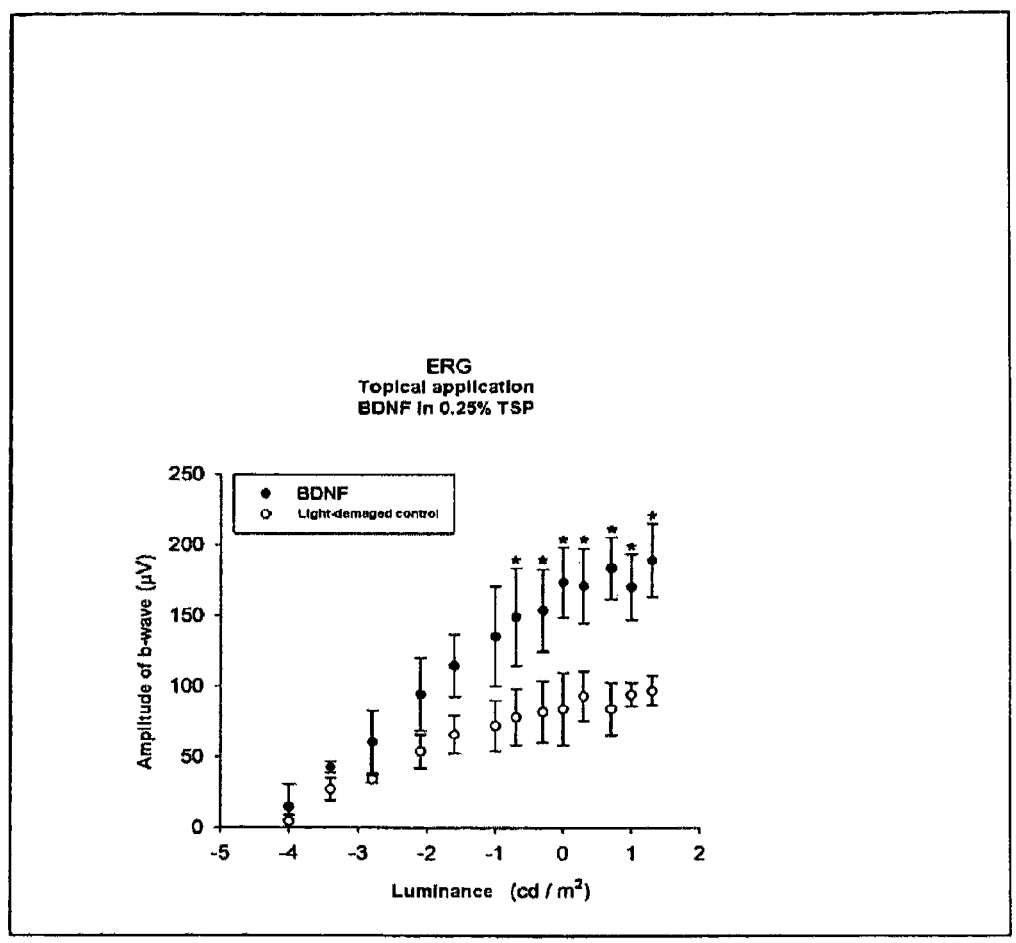

FIG. 6—Topical application of BDNF in TSP reduces light-damage induced alterations of the retinal flash response (flash ERG). The amplitude (µV, see y-axis) of the b-wave of the electroretinogram evoked by flashes of different luminances ($cd/m^2$, see x-axis) and recorded by the eye treated with BDNF (black symbols) or the control eye treated with TSP only (light-damaged control, white symbols) was measured; * indicates that the differences are significant.

Figure 7:
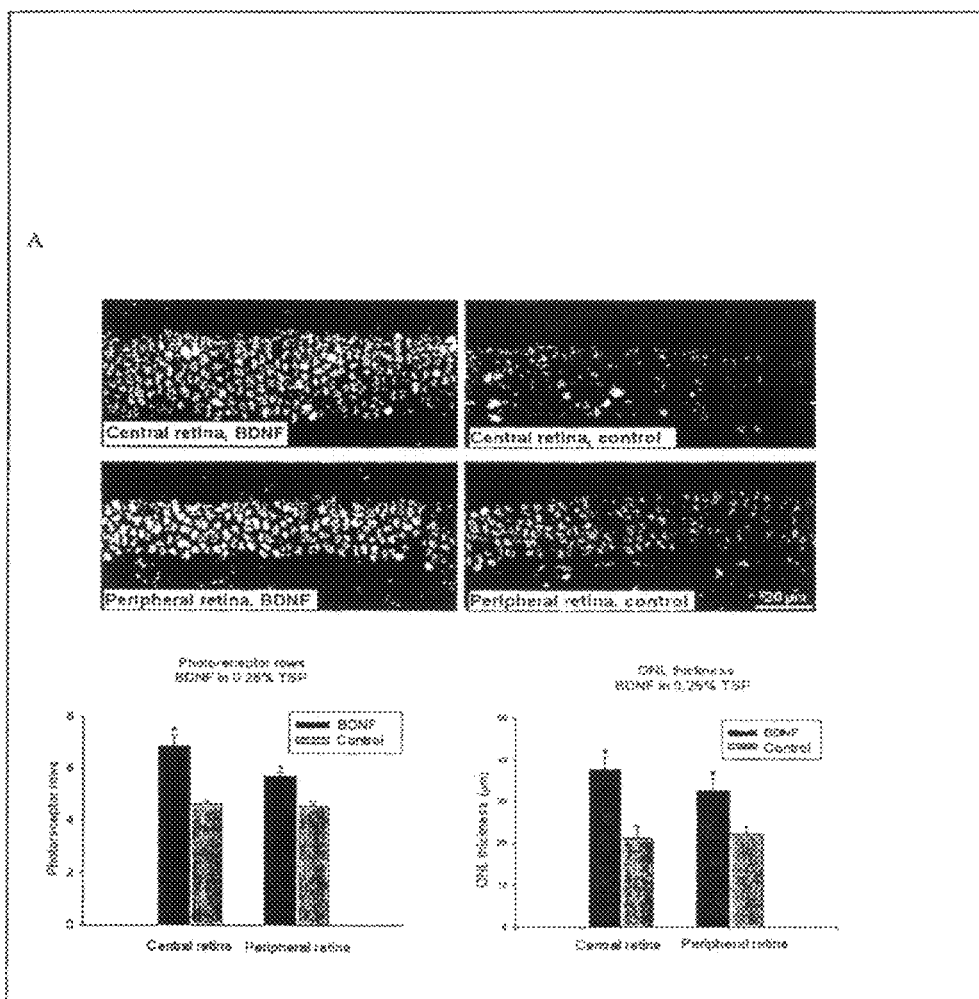

FIG. 7—Topical treatment with BDNF in TSP increases the number of photoreceptors surviving light damage. The photoreceptors are labelled with propidium iodide in cross-sections of retina. Regardless of the method used (photoreceptor cell body row count (FIG. 7B) or measurement of thickness of the outer nuclear layer (ONL) (FIG. 7C)), the photoreceptors present in the central and peripheral retina are significantly (*) more numerous in the eye treated with BDNF than the eye treated with the carrier (control).

Figure 8:
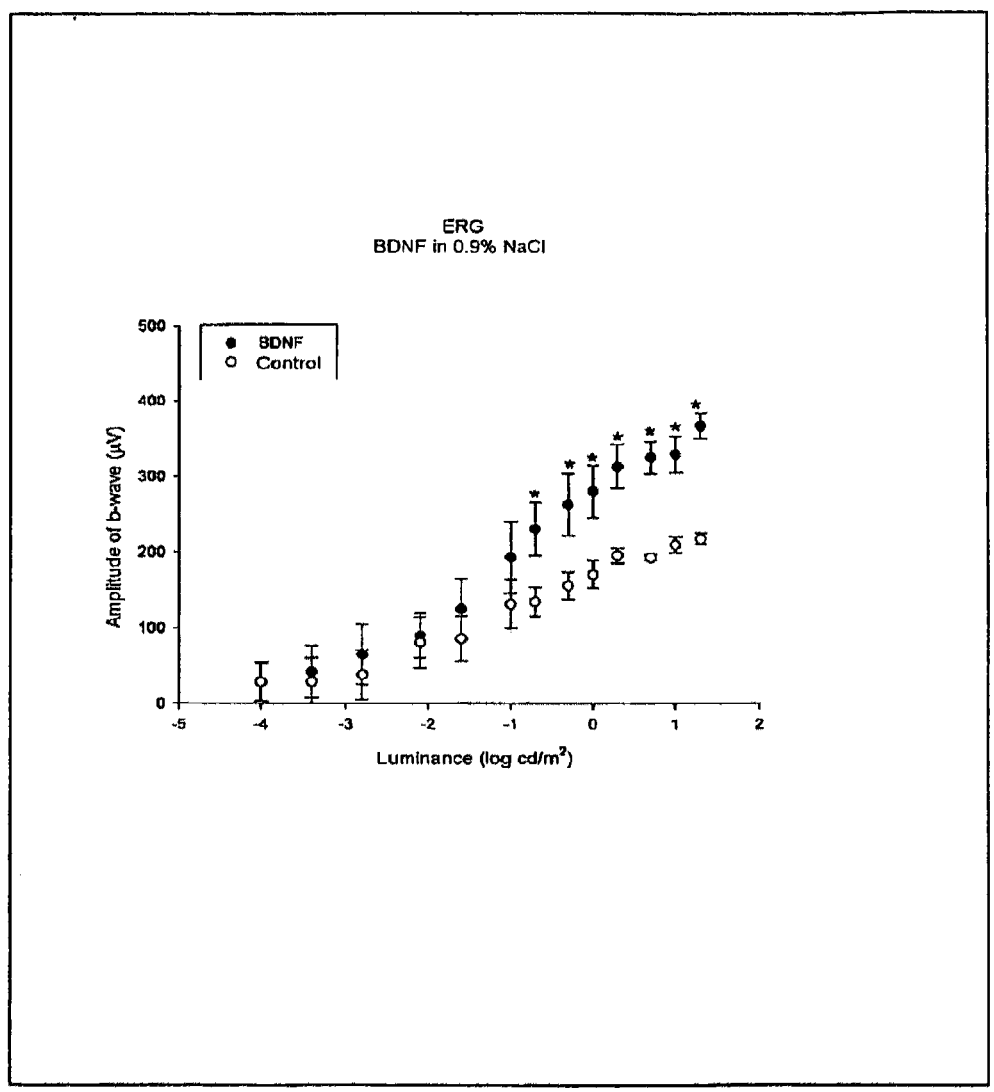

FIG. 8—Topical application of BDNF in saline solution (NaCl) reduces light-damage induced impairment in the retinal response to light. For an explanation of conventions and symbols, see FIG. 6.

Figure 9:
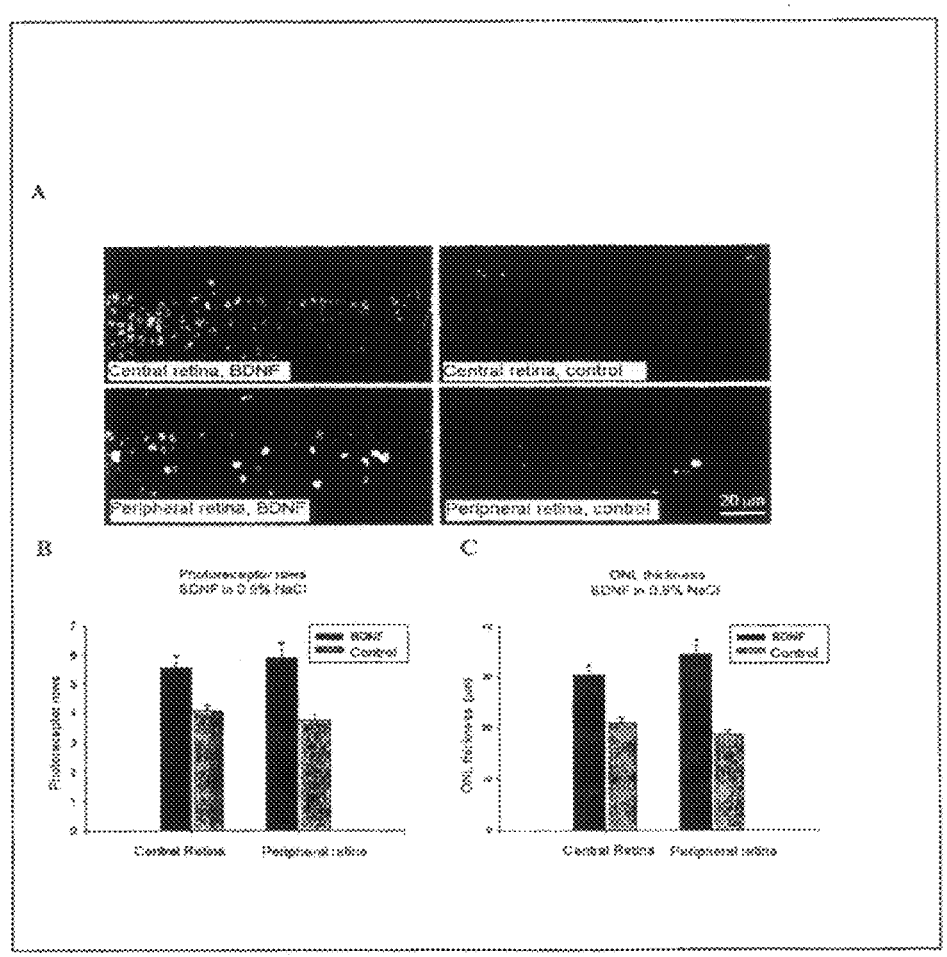

FIG. 9—Topical treatment with BDNF in saline solution increases photoreceptor survival after light damage. For conventions and symbols, see FIG. 7.

Figure 10:
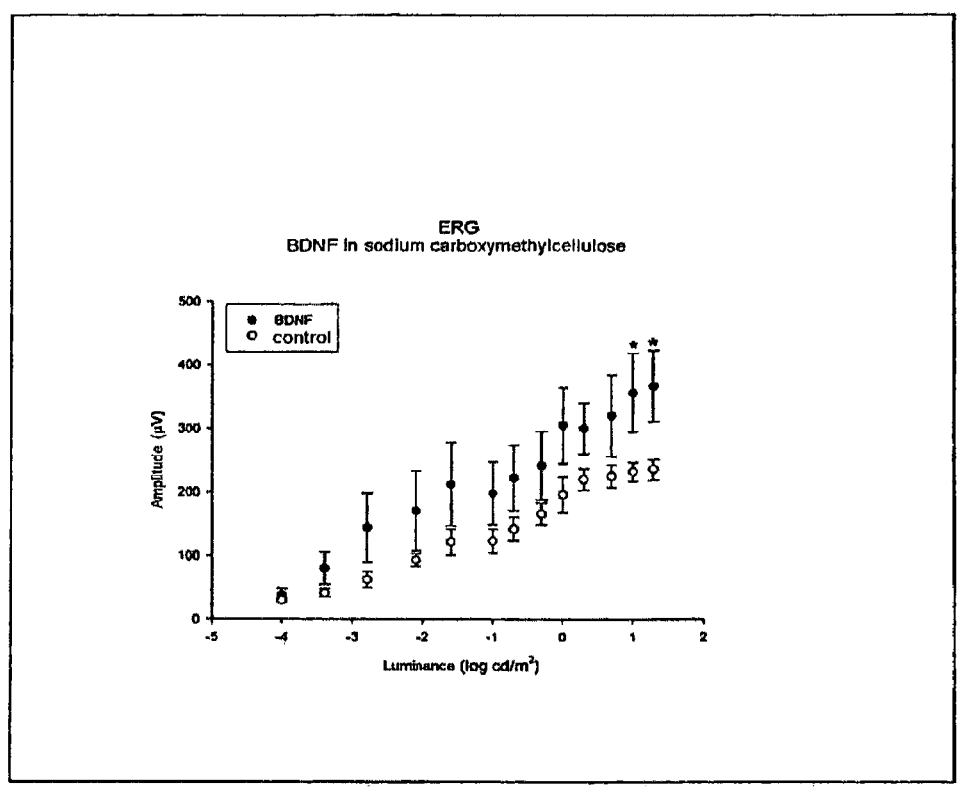

FIG. 10—Topical application of BDNF in solution with sodium carboxymethylcellulose, and impaired response to light induced by light damage. For conventions and symbols, see FIG. 6.

Figure 11:
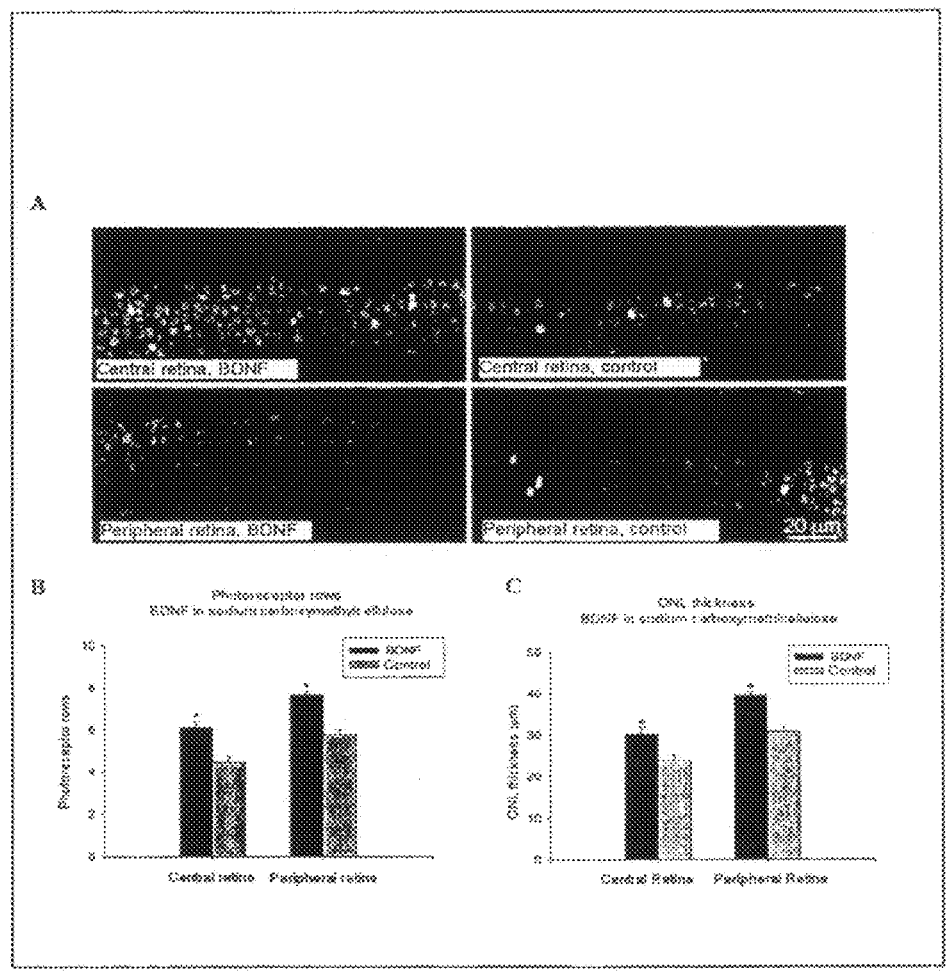

FIG. 11—Effects of topical treatment with BDNF in solution with sodium carboxymethylcellulose on photoreceptor survival after light damage to the eye treated with BDNF and the eye treated with the carrier (control). For conventions and symbols, see FIG. 7.

Figure 12:
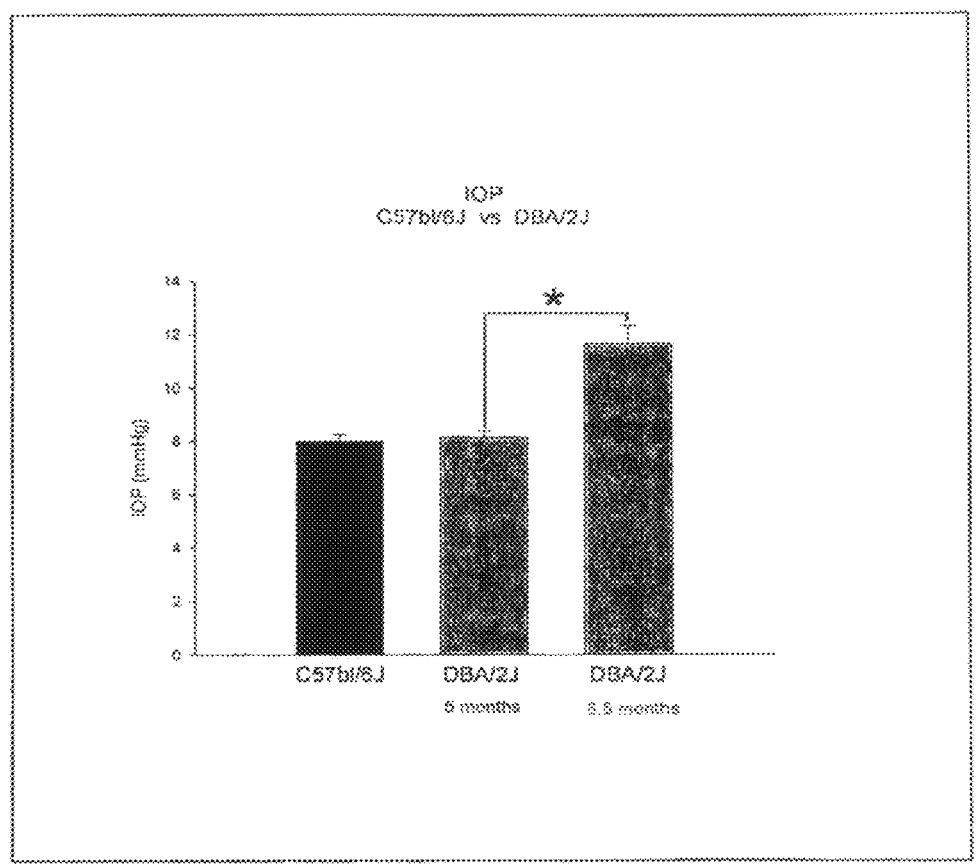

FIG. 12—Increase in intraocular pressure (TOP, mmHg) in an experimental murine glaucoma model, DBA/2J mouse v. normal mouse (C57b1/6J). The increase in TOP in DBA/2J is significant (*) as from the age of 6½ months.

Figure 13:
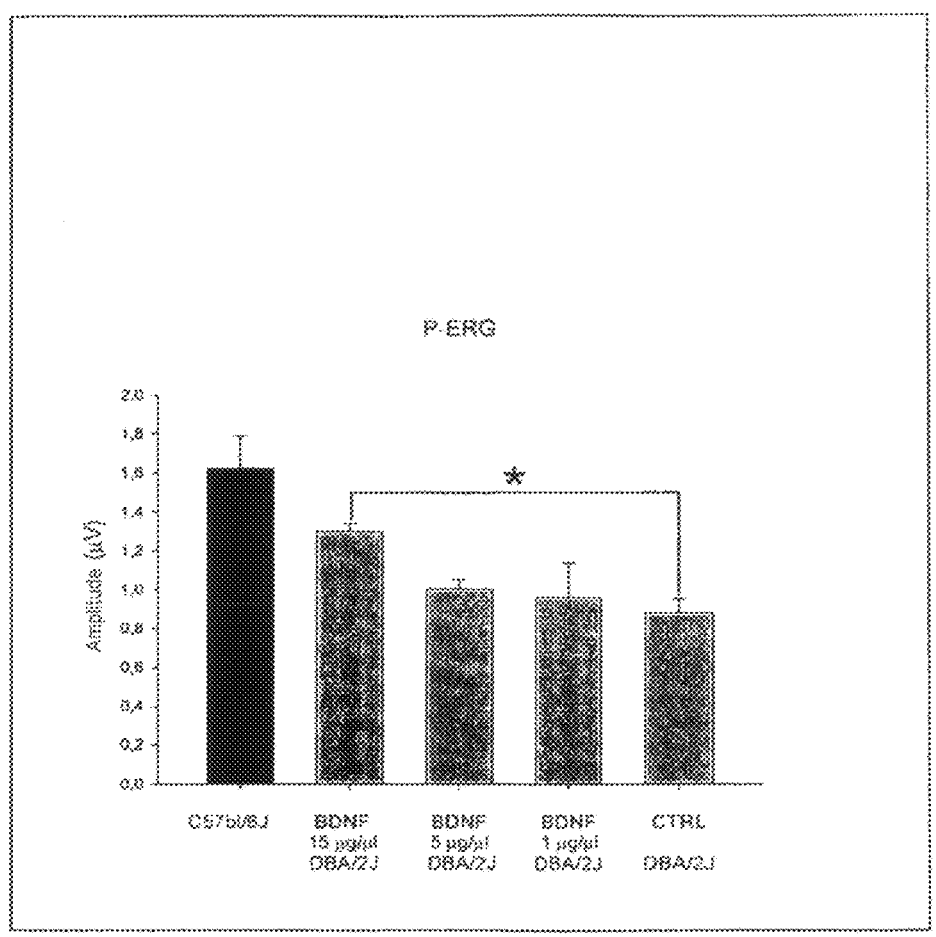

FIG. 13—The response of the retina to visual patterns (pattern ERG, P-ERG; stimulus consisting of a spatial frequency=0.2 C/deg, contrast 90%) was recorded in normal mice (C57b1/6J, dark bar) and glaucoma-developing mice (DBA/2J); the amplitudes of the responses of P-ERG (µV, see y-axis) were measured by stimulating the eye treated for two weeks with different concentrations of BDNF (1, 5 and 15 µg/µl) and by stimulating the eye treated with the carrier, considered as control eye (CTRL); * indicates the significance of the differences. P-ERG was recorded at the age of 7 months in the DBA/2J mouse, ie. after the increase in intraocular pressure (TOP).

Figure 14:
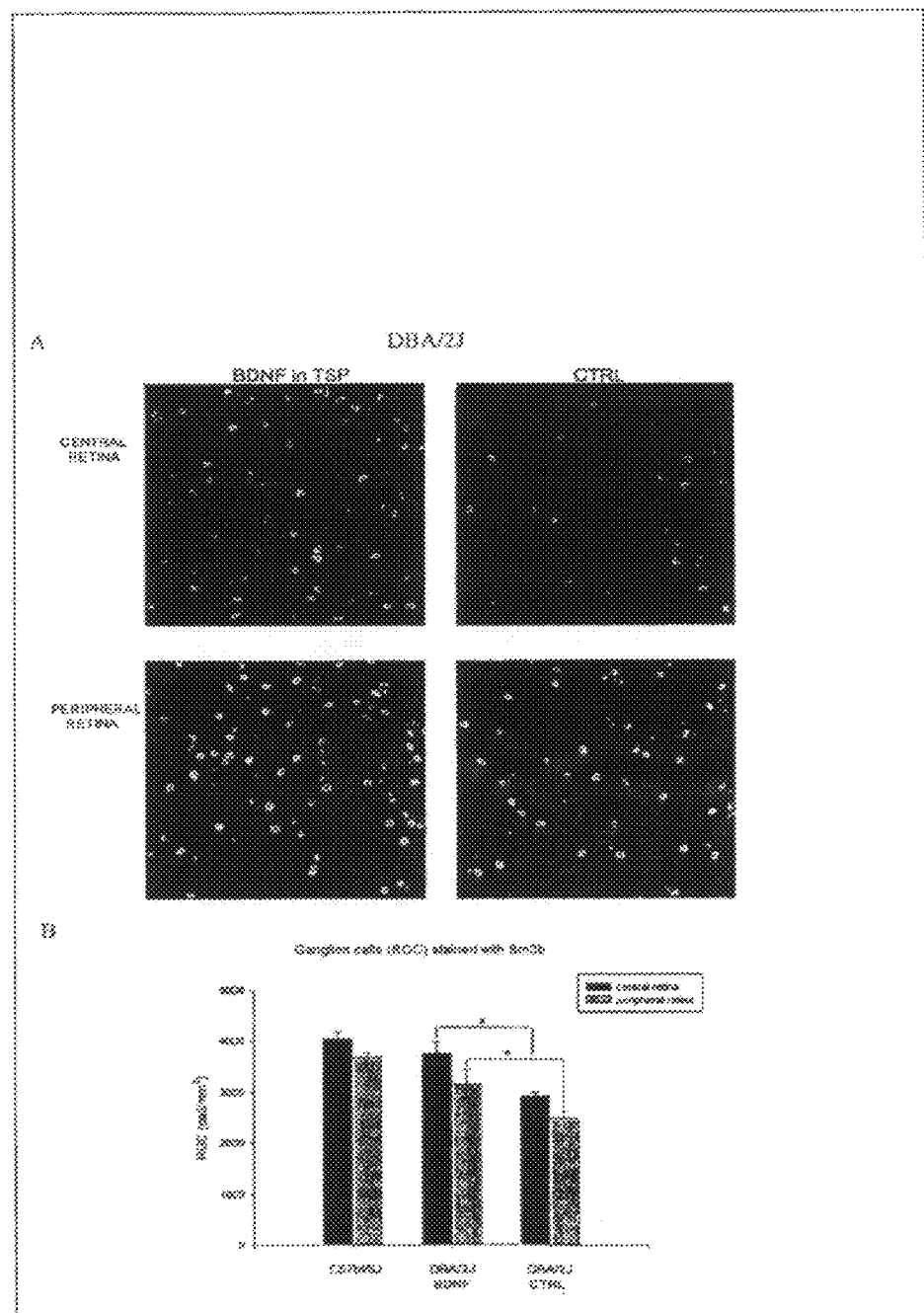

FIG. 14—Retinal ganglion cells (whole-mount preparation) of glaucoma-developing DBA/2J mouse (aged 7 months), labelled with a fluorescent antibody that binds to a transcription factor (Brn3b). A. The left-hand column shows the effects of two weeks' topical treatment with BDNF in TSP in the central retina (top row) and peripheral retina (bottom row). Following treatment with BDNF (left-hand column), the labelled cells were more numerous than in the retina of the control eye (CTRL), which was treated with the carrier only (right-hand column). B. Quantitation of effects of topical treatment with BDNF on ganglion cells (density measured in cells/mm$^2$, shown on the y-axis) labelled with Brn3b in the glaucoma-developing mouse (DBA/2J; eye treated with BDNF; eye treated with carrier, CTRL) and in the normal mouse (C57b1/6J).

DETAILED DESCRIPTION OF THE INVENTION

It has surprisingly been found that by administering exogenous brain-derived neurotrophic factor (BDNF), applied topically to the intact eye surface, in particular in the conjunctival sac, BDNF performs a neuroprotective effect on the retinal cells at both functional and morphological levels, thus allowing the prevention and/or treatment of neurodegenerative retinal disorders.

BDNF has demonstrated neuroprotective efficacy not only towards the photoreceptors, but also towards the ganglion cells, ie. the cells of (i) innermost layer of the retina, which send their fibres to the visual centres, (ii) the optic nerve fibres, and (iii) the extra-retinal visual centres, such as the lateral geniculate body.

The present invention relates to an ophthalmic preparation containing BDNF (Brain-Derived Neurotrophic Factor).

Said ophthalmic preparation contains BDNF in a concentration which can range between the lower limit of 15 µg/µl and 200 µg/µl, preferably between 20 and 100 µg/µl, and even more preferably between 30 and 50 µg/µl. The total bioavailable dose can be between 50 and 4000 µg per administration, according to the volume of the ophthalmic formulation administered and the species to which the treated eye belongs, including humans.

BDNF can be administered alone or in combination with other active ingredients, such as β-blockers, prostaglandins and carbonic anhydrase inhibitors.

The preparation is made in the form of eyedrops, and can be a solution, a suspension, a gel or an ophthalmological ointment with the active ingredient BDNF, or active ingredients, in a pharmaceutically acceptable carrier compatible with the active ingredient and tolerated by the eyes.

The pharmaceutically acceptable carrier can be a saline solution, preferably containing 0.9% of sodium chloride.

It has also been found that the absorption levels of improved BDNF can be increased if at least one pharmaceutically acceptable carrier is used in the preparation, preferably a galactoxyloglucan extracted from tamarind seeds (TSP) which, due to its viscosity, allows a longer BDNF residence time on the eye surface than administration in saline solution, which is washed away from the conjunctiva more quickly.

The TSP concentration can vary, preferably from 0.05 to 2% (weight/volume—w/v), and even more preferably from 0.25 to 0.5% (w/v).

TPS is transparent, viscoelastic and sterile, and is used for corneal protection. TSP also forms a long-lasting film on the eye surface, which lubricates and moistens the cornea and conjunctiva.

According to a further preferred aspect, the viscosified solution contains hyaluronic acid, and even more preferably, hyaluronic acid combined with TSP.

The hyaluronic acid concentration can vary, preferably from 0.05% to 0.8%% (w/v), and even more preferably from 0.2 to 0.4% (w/v).

According to a preferred embodiment, the preparation can include BDNF in the concentration of 15 µg/µl in a saline solution containing 0.9% NaCl.

According to a further preferred embodiment, the preparation can contain BDNF in the concentration of 15 µg/µl in saline solution with TSP, preferably an 0.25% solution.

The eyedrop preparation can be administered topically directly to the intact eye surface, ie. in a non-invasive way, avoiding the use of invasive methods such as intraocular, subretinal and retrobulbar injections. In particular, the preparation can be administered into the conjunctival sac. The preparation can also be formulated as an eyepatch or in contact lenses.

The retina is a partly separate part of the central nervous system; various types of barrier exist, including the blood-retinal barrier, which prevents the non-specific diffusion of compounds such as large molecules to the retina. The intraocular penetration of pharmacologically active compounds applied topically is regulated by barriers located in the cornea and the conjunctiva, by systemic absorption and by metabolic breakdown effected by the enzymes present in those tissues. Once instilled, the pharmacologically active compounds must cross a complex system of blood barriers, including the blood-retinal barrier, to penetrate the underlying tissues as far as the retina.

Moreover, the retina, through the ganglion cells, from which the optic nerve fibres originate, is connected via the optic nerve to visual centres such as the dorsal part of the lateral geniculate body (dLGN).

As demonstrated in the experimental part, BDNF, when administered topically according to the invention, can be conveyed to the retina, inducing an increase in its retinal concentration to levels which perform neuroprotective effects from both the functional and the morphological standpoint.

It has also surprisingly been found, as demonstrated by experimental evidence, that the ganglion cells allow anterograde transport of BDNF, allowing BDNF to prevent and treat degeneration not only of the ganglion cells but also of the optic nerve fibres, and extension of the disorder to the extra-retinal visual centres, such as the lateral geniculate body.

The present invention also relates to the use of BDNF to prepare an ophthalmic medicament in the form of eyedrops for topical administration to the intact eye surface for the prevention and/or treatment of neurodegenerative disorders of the retina, optic nerve and lateral geniculate body, in particular degenerative retinopathies (such as retinitis pigmentosa and glaucoma), age-related retinopathies (such as age-related macular degeneration), vascular and proliferative disorders of the retina, detachment of the retina and retinopathy of prematurity (ROP) and diabetic retinopathy, which lead to blindness. The preparations according to the invention are useful for the prevention and/or treatment of neurodegenerative disorders of the retina, optic nerve and lateral geniculate body, especially, for example, retinitis pigmentosa and glaucoma (including congenital glaucoma, infantile glaucoma, juvenile glaucoma, adult glaucoma, primary open-angle glaucoma, primary angle-closure glaucoma, acute glaucoma, iatrogenic glaucoma and secondary glaucoma).

Glaucoma is one of a series of progressive disorders affecting the eye which, if not suitably treated, lead to blindness due to loss of ganglion cells and progressive atrophy of the optic nerve fibres.

Glaucoma is characterised by an increase in intraocular pressure (TOP) which can damage the ganglion cells and the optic nerve fibres either directly (mechanically) or indirectly by inducing ischaemia of the retinal vessels that supply the inner retina. At the progressive stage, as well as the retina, glaucoma can affect the visual centres, such as the lateral geniculate body, until the visual cortex is eventually involved.

It has also been found that treatment with BDNF in effective concentrations not only prevents and reduces photoreceptor degeneration induced by prolonged exposure to light (light damage) and preserves the retinal response to light; moreover, the use of an experimental glaucoma model demonstrates that topical application of BDNF prevents the degeneration of the retinal ganglion cells which results from a rise in intraocular pressure (IOP) in an animal glaucoma model; in both animal models, BDNF did not alter the retinal response to visual stimuli.

The examples given below further illustrate the invention.

EXAMPLES

Examples of Preparations

Preparation 1—BDNF in saline solution: 150 µg of BDNF is dissolved in 10 µl of saline solution containing 0.9% NaCl;

Preparation 2—BDNF in saline solution with sodium carboxymethylcellulose: 150 µg of BDNF is dissolved in a solution consisting of 5 µl of saline solution containing 0.9% NaCl and 5 µl of 0.4% sodium carboxymethylcellulose.

Preparation 3—BDNF in saline solution with TSP: 150 µg of BDNF is dissolved in 5 µl of saline solution containing 0.9% NaCl and 5 µl of 0.5% TSP.

Preparation 4—BDNF in saline solution with hyaluronic acid (0.2%): 150 µg of BDNF is dissolved in 5 µl of saline solution containing 0.9% NaCl and 5 µl of 0.4% hyaluronic acid.

Preparation 5—BDNF in saline solution with hyaluronic acid (0.4%): 150 µg of BDNF is dissolved in 5 µl of saline solution containing 0.9% NaCl and 5 µl of 0.8% hyaluronic acid.

Preparation 6—BDNF in saline solution with hyaluronic acid and TSP (I): 150 µg of BDNF is dissolved in 5 µl of saline solution containing 0.9% NaCl and 5 µl of 0.4% hyaluronic acid and 0.4% TSP.

Preparation 7—BDNF in saline solution with hyaluronic acid and TSP (II): 150 µg of BDNF is dissolved in 5 µl of saline solution containing 0.9% NaCl and 5 µl of 0.8% hyaluronic acid and 0.4% TSP.

Preparation 8—BDNF in saline solution with hyaluronic acid and TSP (II): 150 µg of BDNF is dissolved in 5 µl of saline solution containing 0.9% NaCl and 5 µl of 0.4% hyaluronic acid and 0.6% TSP.

Bioassays 2.1 Example

Determination of BDNF Levels in Vitreous Humour, Retina and Optic Nerve After 6 Hours' Topical Treatment of the Eye with BDNF-Based Preparations Preparations 1, 2 and 3 Containing BDNF, as Described Above, were Used:

The test was conducted on albino rats (Wistar rats, Harlan, Italy); BDNF in saline solution with sodium carboxymethylcellulose, or in saline solution with TSP, was applied topically, being instilled into the conjunctival sac of one eye, while the other eye, used as control, was treated with the solution ("placebo") used to include and carry BDNF.

Determination of BDNF Levels in the Retina, Vitreous Humour and Optic Nerve

The animals were killed 6 hours after the application, after induction of deep anaesthesia with an intraperitoneal urethane injection (20%). The eye was then removed, and the BDNF level measured in the vitreous humour, retinal homogenate and homogenate of optic nerve of both the eye treated with BDNF and the other eye treated with the carrier solution only (control eye). The measurements were conducted by immunoassay (ELISA; BDNF Emax immunoassay system, Promega, Madison, Wis., USA). The quantity of BDNF in the optic nerve was also determined, to establish whether BDNF introduced from the exterior by topical application was taken up and conveyed by the retinal cells, in particular by the retinal ganglion cells which, with their fibres, form the optic nerve.

The results shown in the chart in FIG. 1 were obtained with a topical application of BDNF in saline solution (0.9% NaCl), and are expressed as mean BDNF concentration values in the retina (A), optic nerve (B) and vitreous humour (C), expressed as pg/mg of protein.

The statistical analysis was conducted with Student's t-test, comparing the eye treated with BDNF with the control eye: in all cases, the differences between the treated eye and the control eye were statistically significant (*, $p<0.05$).

The results shown in the charts in FIG. 2 relate to a topical application of BDNF in solution with sodium carboxymethylcellulose (0.2%), while the results shown in the charts in FIG. 3 were obtained with a topical application of BDNF in solution with TSP (0.25%); in both cases, the statistical analysis was conducted with Student's t-test, comparing the eye treated with BDNF with the control eye. In all cases, the differences between the treated eye and the control eye were statistically significant (*, $p<0.05$).

FIG. 4 shows the comparative levels of BDNF in the retina for each type of solution/carrier used; this analysis makes it easier to compare the efficacy of the different solutions/carriers at the same BDNF concentration (10 µl of solution containing 150 µg of BDNF). Topical treatment with BDNF in TSP produced significantly higher retinal levels of BDNF than the other two formulations used, ie. BDNF in saline solution and BDNF in solution with sodium carboxymethylcellulose (Student's t-test *, $p<0.05$). Topical treatment with BDNF in solution with sodium carboxymethylcellulose proved to be the least effective in increasing the retinal BDNF level.

2.2 Example

Determination of BDNF Levels in the Retina, Vitreous Humour and Optic Nerve at Different Times After Topical Treatment of the Eye with BDNF in TSP The extent to which BDNF remained high in the retina, vitreous humour and optic nerve after a single topical application was studied. This study was conducted with the carrier containing TSP, which proved the most effective in facilitating the transscleral passage of BDNF to the retina, optic nerve and vitreous humour. The kinetics of the BDNF levels in the retina, optic nerve and vitreous humour after topical treatment of the eye were then studied, using TSP. N=5 eyes were treated in each test group. The BDNF concentration in the retina, optic nerve and vitreous humour was measured at different intervals of time after application of an 0.25% solution of TSP containing BDNF (10 µl of a solution containing 150 µg of BDNF). The control eye was treated only with the carrier solution containing 0.25% TSP. This experiment was performed to establish the time trend of the BDNF levels after a single topical application. The charts show the mean BDNF values (y-axis; pg/ml) in the retina, optic nerve and vitreous humour 6, 12 and 24 hours after the application. FIG. 5 shows that the BDNF level in the retina remains statistically high, returning to baseline levels in 12-24 hours. The statistical analysis was conducted with Student's t-test: in A *, p<0.01 compared with the control eye. The results of this experiment suggest that in long-term treatment with BDNF, carried in artificial tears, in particular based on TSP, one topical application every 12 hours is sufficient to maintain high BDNF levels in the retina.

2.3 Example

Neuroprotective Effects of Topical Application of BDNF-Based Preparations

To establish the neuroprotective effects of BDNF after treatment by topical application in the conjunctival sac, an experimental model in which retinal degeneration is induced by light damage was used in animal models; this model is widely used to study degeneration of the retinal photoreceptors induced by lengthy exposure to a strong light source (La Vail et al., 1987; Rex et al., 2003). Photoreceptor death takes place by apoptosis, and is caused by excessive absorption of photons by the visual pigment rhodopsin, leading to alteration of the pigment regeneration cycle which eventually involves the pigmented epithelium cells. The experimental animal model tested was the albino rat (Surace et al., 2005), in view of the marked sensitivity of its photoreceptors to light. The experimental protocol used was modified (Rex et al., 2003) and expanded from that originally proposed by LaVail's group (LaVail et al., 1987).

The following BDNF-based preparations were used:
a) BDNF in 0.25% TSP solution (10 µl of a solution containing 150 µg of BDNF).
b) BDNF in saline solution (0.9% NaCl—10 µl of a solution containing 150 µg of BDNF).
c) BDNF in an 0.2% solution of sodium carboxymethylcellulose (10 µl of a solution containing 150 µg of BDNF).

The eyes of rats were treated with the preparations listed above, and the rats were subjected to light damage. The control eyes were treated with the carrier solution only. N=4 eyes were treated in each test group. In particular, after 6 hours' treatment (eye treated with BDNF and control eye treated with carrier solution only), these rats were subjected to lengthy exposure to light for 48 hours (animal light-damage model, light source intensity 1000 lux). This lengthy exposure to light induces degeneration of many of the photoreceptors in the retina of albino rats. The neuroprotection exerted by BDNF was verified by morphological methods, designed to evaluate the survival of the photoreceptors, and functional methods, by recording the retinal response to light (flash electroretinogram [ERG], which is widely used to evaluate the functional state of the external retina in patients suffering from retinal disorders). In view of the small number of cones in the rat, forming the basis of the ERG response under photopic conditions, and the reduced amplitude of the ERG in photopic conditions in the albino rat, only the flash ERG was recorded under scotopic adaptation conditions, expressing the response of the rods of which the rat retina is mainly composed. The flash ERG (scotopic) was recorded 7 days after the end of the light-damage period.

Preparation a)
FIG. 6 shows the amplitude of the b-wave of the flash ERG according to luminance under scotopic adaptation conditions. As clearly shown in the chart in FIG. 6, BDNF in TSP, applied topically, significantly reduces the effects of light damage on the retinal response to flashes (flash ERG). In fact, the amplitudes (mean amplitude values expressed in µV) of the eye treated with BDNF are significantly greater than those of the control eye, *, p<0.05 (one-way ANOVA).

Preparation b)
FIG. 8 shows the amplitudes of the b-wave according to luminance under scotopic adaptation conditions. The results indicate that BDNF in saline solution is also able to reduce the alterations of the retinal response to light induced by light damage (flash ERG). The amplitudes of the b-wave in the light-damaged eyes of rats treated with BDNF are greater than those recorded for the control eye; the amplitudes (mean amplitude values expressed in µV) of the eye treated with BDNF in saline are significantly greater than those of the control eye, *, p<0.05 (one-way ANOVA).

Preparation c)
FIG. 10 shows the amplitude of the b-wave according to luminance under conditions of adaptation to darkness. The figure demonstrates that the amplitudes (mean amplitude values expressed in µV) of the eye treated with BDNF in solution with sodium carboxymethylcellulose are only significantly greater than those of the control eye, *, p<0.05 (one-way ANOVA) at the highest luminance values. In conclusion, in terms of functional recovery of the retinal response to light, sodium carboxymethylcellulose proved less effective than TSP and saline solution in preventing impairment of the retinal response to light.

Subsequently, the effects of topical treatment with the BDNF-based preparations listed above on degeneration of the retinal photoreceptors were evaluated in the retinas of the eyes whose flash ERG was recorded.

The effects of topical treatment with BDNF on photoreceptor degeneration were quantified by counting the rows of photoreceptors that survived the light damage and measuring the thickness of the retinal outer nuclear layer (ONL) which contains the photoreceptor cell bodies. To perform those measurements, the photoreceptor nuclei were labelled with propidium iodide.

Preparation a)
The results obtained are shown in FIG. 7. FIG. 7A shows the retinal cross-sections of the eye treated with BDNF (in 0.25% TSP) and the control eye. To perform those measurements, the photoreceptor nuclei were labelled with propidium iodide. Regardless of the method used (count of photoreceptor cell body rows (FIG. 7B) or thickness of the outer nuclear layer (ONL) (FIG. 7C)), the photoreceptors present in the central and peripheral retina are significantly (Student's t-test *, p<0.001) more numerous in the eye treated with BDNF than the eye treated with the carrier (control).

It was then demonstrated that BDNF in TSP, when applied topically in the conjunctival sac, protects the retina from light damage.

Preparation b)
FIG. 9 (A) shows the retinal cross-sections of the right eye treated with BDNF (in saline solution, 0.9% NaCl) and the left (control) eye treated with saline solution only. The effects of topical treatment with BDNF on photoreceptor degeneration were quantified by counting the rows of cell bodies of the photoreceptors that survived the light damage (FIG. 9B) or measuring the thickness of the retinal outer nuclear layer (ONL) which contains the photoreceptor cell bodies (FIG. 9C). The differences between the retinas of the treated eye and the control eye (count of photoreceptor rows or ONL thickness) proved significant in both the central and the peripheral retina (Student's t-test *, p<0.001).

Topical treatment with BDNF in saline increases the number of photoreceptors that survive light damage in the eye compared with the control eye.

Preparation c)

Finally, the effects of topical treatment with BDNF (in solution with sodium carboxymethylcellulose) on photoreceptor degeneration were quantified by measuring the rows of cell bodies of the photoreceptors that survived the light damage (FIG. 11B) and the thickness of the outer nuclear retina (ONL) which contains the photoreceptor cell bodies (FIG. 11C).

Considering the results obtained, in terms of functional recovery and prevention of photoreceptor degeneration following light damage, it can be concluded that topical treatment with BDNF in TSP and in saline solution exercises neuroprotective effects against light damage, whereas treatment with BDNF in solution with sodium carboxymethylcellulose is less effective at the same BDNF concentration.

It was also demonstrated that treatment with BDNF does not induce functional alterations in the retina, impairing its response to visual stimuli.

2.4 Example

Neuroprotective Effects Induced by Repeated Topical Application of BDNF in an Experimental Glaucoma Model Glaucoma is a degenerative disorder of the retina which has various causes, and presents in different forms (it is classified on the basis of age as congenital glaucoma, infantile glaucoma, juvenile glaucoma or adult glaucoma; and on the basis of etiopathogenesis as primary glaucoma: primary open-angle glaucoma or primary angle-closure glaucoma; and secondary glaucoma induced by other disorders, including iatrogenic glaucoma). The most common form of glaucoma, namely primary open-angle glaucoma (POAG), is characterised by increased intraocular pressure which causes dysfunction and subsequent degeneration of the ganglion cells associated with atrophy of the optic nerve; the symptoms are gradual loss of vision, culminating in blindness. The mechanism that causes the dysfunction and degeneration of the ganglion cells, with atrophy of the optic nerve, is not yet entirely clear, although the prevalent hypothesis is that increased intraocular pressure (TOP) induces mechanical damage to the optic nerve fibres in the lamina cribrosa, and an ischaemic alteration of the head of the optic nerve and the inner retina. In recent years, pharmacological treatment has aimed at reducing the IOP, although a considerable number of patients are resistant to the current pharmacological treatment and suffer progressive, irreversible loss of the visual function. There are currently no drugs designed to achieve neuroprotection of the retinal ganglion cells and the optic nerve fibres in order to prevent reduction of visual capacity and restore normal eyesight. In the present patent, we propose the use of topical treatments with BDNF in the conjunctival sac to increase the retinal BDNF levels in a stable way so as to counteract the progressive dysfunction of the ganglion cells, followed by their degeneration and death. This proposal is partly based on the demonstration that the BDNF receptor, called TrkB, is expressed in the ganglion cells (Jelsma et al., 1993). To verify our hypothesis we used the most common experimental model of spontaneous glaucoma, a double mutant mouse called DBA/2J (John et al., 1998; Chang et al., 1999). The DBA/2J mouse presents homozygous mutations of two separate genes; the first is tyrosine-related protein (Tyrp1-/-) coding for a melanosome protein, and the second is a membrane glycoprotein (Gpnmb-/-). This mouse is characterised by a progressive increase in intraocular pressure with progressive loss of the retinal response to structured visual stimuli, which depends on the inner retina/ganglion cells; in humans and in the animal model, this retinal response is called the pattern electroretinogram (P-ERG; Domenici et al., 1991; Ventura and Porciatti, 2006; Falsini et al., 2008). The dysfunction of the ganglion cells is followed by a degeneration of said cells with progressive atrophy of the optic nerve fibres (Ventura et al., 2006). As shown in FIG. 12, in this murine glaucoma model (DBA/2J), the TOP starts to increase after 5 months of postnatal life: at 6½ months the TOP in the DBA/2J mouse (N=10) already appears significantly higher (t-test;* p<0.05) than that measured in the normal mouse (C57b1/6J; N=5) and in the DBA/2J mouse at the age of 5 months (N=9). The chart in FIG. 13 shows the amplitudes of the response of the inner retina/ganglion cells (P-ERG) to structured visual stimuli (the visual patterns used as stimulus were luminance profiles with spatial frequency=0.2 C./deg and 90% contrast), recorded with corneal electrodes connected to an amplifier and to a computer for on-line analysis. As shown in FIG. 13, the P-ERG is already altered in the DBA/2J mouse (CTRL, N=4) at the age of 7 months (significant reduction in P-ERG amplitudes; Student's t-test, * p<0.05). From the age of 6.5 months, ie. from the time when the TOP was stably increased (FIG. 12), a two-week treatment was performed involving repeated topical applications of BDNF in TSP (one treatment every 48 hours) in one eye, and the carrier in the other (control eye). Three different BDNF concentrations were used (N=4 DBA/2J mice per group): 1, 5 and 15 µg/µl. As shown in the histogram, topical treatment with BDNF at the concentration of 15 µg/µl (150 µg in 10 µl of solution containing 0.25% TSP, ophthalmic preparation a), but not at concentrations of 1 and 5 µg/µl, prevented P-ERG alterations in the DBA/2J mouse (compare the data of the treated eye with the control eye; Student's t-test, * p<0.05). To establish whether a P-ERG alteration corresponds to an alteration of the ganglion cells, labelled with immunohistochemical methods, we used a transcription factor, Brn3b, expressed in the ganglion cells; mutant mice (Brn3b -/-) for this factor are associated with an alteration of the ganglion cells (Badea et al., 2009). FIG. 14 A shows enlargements of retinal preparations in which the ganglion cells are labelled green with a fluorescent antibody and analysed by confocal microscopy. The number of labelled ganglion cells is clearly smaller in the eye of the DBA/2J mouse, in both the central and the peripheral retina. FIG. 14 B shows the quantitation of the labelled cells in terms of density (cells/mm$^2$). Two weeks' treatment with BDNF in TSP at the concentration of 15 µg/µl prevented the reduction in cells labelled with Brn3b compared with the control eye treated with the carrier only (Student's t-test, * p<0.05).

The data reported lead to the conclusion that repeated topical treatments with BDNF prevent functional alterations of the ganglion cells and restore the retinal visual capacity in an experimental glaucoma model. The minimal effective concentration of BDNF able to exert protective effects on the function of the ganglion cells is 15 µg/µl.

BIBLIOGRAPHY

Badea T C, Cahill H, Ecker J, Hattar S, Nathans J. Distinct roles of transcription factors brn3a and brn3b in controlling the development, morphology, and function of retinal ganglion cells. Neuron. 2009 Mar. 26; 61(6):852-64.

Bennett J L, Zeiler S R & Jones K R (1999) Patterned expression of BDNF and NT-3 in the retina and anterior segment of the developing mammalian eye. *Invest Ophthalmol Vis Sci* 40, 2996-3005.

Burgalassi S, Raimondi L, Pirisino R, Banchelli G, Boldrini E, Saettone M F. Effect of xyloglucan (tamarind seed polysaccharide) on conjunctival cell adhesion to laminin and on corneal epithelium wound healing. Eur J Ophthalmol. 2000 January-March; 10(1):71-6.

Calamusa M, Pattabiraman P P, Pozdeyev N, Iuvone P M, Cellerino A, Domenici L (2007) Specific alterations of tyrosine hydroxylase immunopositive cells in the retina of NT-4 knock out mice. Vision Res. 47, 1523-1536.

Caleo M, Medini P, von Bartheld C S, Maffei L (2003) Provision of Brain-Derived Neurotrophic Factor via Anterograde Transport from the Eye Preserves the Physiological Responses of Axotomized Geniculate Neurons. *J Neurosci* 23, 287-296.

Cellerino A, Carroll P, Thoenen H & Barde Y A. (1997) Reduced size of retinal ganglion cell axons and hypomyelination in mice lacking brain-derived neurotrophic factor. *Mol Cell Neurosci* 9, 397-408.

Cellerino A & Kohler K (1997) Brain-derived neurotrophic factor/neurotrophin-4 receptor TrkB is localized on ganglion cells and dopaminergic amacrine cells in the vertebrate retina. *J Comp Neurol* 386, 149-160.

Chang B, Smith R S, Hawes N L, Anderson M G, Zabaleta A, Savinova O, Roderick T H, Heckenlively J R, Davisson M T, John S W. Interacting loci cause severe iris atrophy and glaucoma in DBA/2J mice. Nat Genet. 1999 April; 21(4): 405-9.

Chytrova G & Johnson J E (2004) Spontaneous retinal activity modulates BDNF trafficking in the developing chick visual system. *Mol Cell Neurosci* 25, 549-57.

Di Polo A, Cheng L, Bray G M & Aguayo A J (2000) Colocalization of TrkB and brain-derived neurotrophic factor proteins in green-red-sensitive cone outer segments. *Invest Ophthalmol Vis Sci* 41, 4014-21.

Domenici L, Gravina A, Berardi N, Maffei L. Different effects of intracranial and intraorbital section of the optic nerve on the functional responses of rat retinal ganglion cells. Exp Brain Res. 1991; 86(3):579-84.

Falsini B, Marangoni D, Salgarello T, Stifano G, Montrone L, Campagna F, Aliberti S, Balestrazzi E, Colotto A. Structure-function relationship in ocular hypertension and glaucoma: interindividual and interocular analysis by OCT and pattern ERG. Graefes Arch Clin Exp Ophthalmol. 2008 August; 246(8): 1153-62.

Garcia M, Forster V, Hicks D, Vecino E. (2003) In vivo expression of neurotrophins and neurotrophin receptors is conserved in adult porcine retina in vitro. Investigative *Ophthalmology and Visual Science* 44, 4532-454155.

Ghelardi E, Tavanti A, Davini P, Celandroni F, Salvetti S, Parisio E, Boldrini E, Senesi S, Campa M. A mucoadhesive polymer extracted from tamarind seed improves the intraocular penetration and efficacy of rufloxacin in topical treatment of experimental bacterial keratitis. Antimicrob Agents Chemother. 2004 September; 48(9):3396-401.

Ghelardi E, Tavanti A, Celandroni F, Lupetti A, Blandizzi C, Boldrini E, Campa M, Senesi S. Effect of a novel mucoadhesive polysaccharide obtained from tamarind seeds on the intraocular penetration of gentamicin and ofloxacin in rabbits. J Antimicrob Chemother. 2000 November; 46(5):831-4.

Hallbook F, Backstrom A, Kullander K, Ebendal T & Carri N G. (1996) Expression of neurotrophins and trk receptors in the avian retina. *J Comp Neurol* 364, 664-76.

Harada T, Harada C, Kohsaka S Wada E, Yoshida k, Ohno S, Mamada H, Tanaka K, Parada L F Wada K (2002) Microglia-Müller glia cell interactions control neurotrophic factor production during light-induced retinal degeneration. *J. Neurosci* 22, 9228-9236.

Herzog K H, Bailey K & Barde Y A. (1994) Expression of the BDNF gene in the developing visual system of the chick. *Development* 120, 1643-9.

Herzog K H & von Bartheld C S (1998) Contributions of the optic tectum and the retina as sources of brain-derived neurotrophic factor for retinal ganglion cells in the chick embryo. *J Neurosci* 18, 2891-906.

Jelsma T N, Friedman H H, Berkelaar M, Bray G M & Aguayo A J. (1993) Different forms of the neurotrophin receptor trkB mRNA predominate in rat retina and optic nerve. *J Neurobiol* 24, 1207-14.

John S W, Smith R S, Savinova O V, Hawes N L, Chang B, Turnbull D, Davisson M, Roderick T H, Heckenlively J R. Essential iris atrophy, pigment dispersion, and glaucoma in DBA/2J mice. Invest Ophthalmol Vis Sci. 1998 May; 39(6):951-62.

Karlsson M & Hallbook F. (1998) Kainic acid, tetrodotoxin and light modulate expression of brain-derived neurotrophic factor in developing avian retinal ganglion cells and their tectal target. *Neuroscience* 83, 137-50.

Lambiase A, Tirassa P, Micera A, Aloe L, Bonini S. (2005) Pharmacokinetics of conjunctivally applied nerve growth factor in the retina and optic nerve of adult rats. *Invest Ophthalmol Vis Sci* 46, 3800-6.

LaVail, M. M., Gorrin, G. M., Repaci, M. A., Thomas, L. A., and Ginsberg, H. M. (1987) Genetic regulation of light damage to photoreceptors. Invest. Ophthalmol. *Visual Sci* 28, 1043-1048.

Levi-Montalcini R. (1987) The nerve growth factor 35 years later. Science 237, 1154-1162.

McGill T G, Prusky G T, Douglas R M, Yasumura D, Matthes M T, Nune G, Donohue-Rolfe K, Yang H, Niculescu D, Hauswirth W W, Girman S V, Lund R D, Duncan J L, LaVail M M (2007) Intraocular CNTF Reduces Vision in Normal Rats in a Dose-Dependent Manner. *IOVS* 48, 5756-5765.

Perez M T & Caminos E (1995) Expression of brain-derived neurotrophic factor and of its functional receptor in neonatal and adult rat retina. *Neurosci Lett* 183, 96-99.

Pollock G S & Frost D O (2003) Complexity in the modulation of neurotrophic factor mRNA expression by early visual experience. *Brain Res Dev Brain Res* 143, 225-32.

Pollock G S, Robichon R, Boyd K A, Kerkel K A, Kramer M, Lyles J, Ambalavanar R, Khan A, Kaplan D R, Williams R W & Frost D O. (2003) TrkB receptor signalling regulates developmental death dynamics, but not final number, of retinal ganglion cells. *J Neurosci* 23, 10137-45. 56.

Reichardt L F (2006) Neurotrophin-regulated signalling pathways. *Phil Trans Royal Soc B* 361, 1471-1492.

Rex T. S., Allocca M., Domenici L., Surace E. M., Maguire A. M., Lyubarsky A., Cellerino A., Auricchio A. (2004) Systemic but not intraocular Epo gene transfer protects the retina from light- and genetic-induced degeneration. *Mol Ther* 10, 855.

Rohrer B, Korenbrot J I, LaVail M M, Reichardt L F & Xu B (1999) Role of neurotrophin receptor TrkB in the maturation of rod photoreceptors and establishment of synaptic transmission to the inner retina. *J Neurosci* 19, 8919-8930.

Seki M, Nawa H, Fukuchi T, Abe H & Takei N (2003) BDNF is upregulated by postnatal development and visual experience: quantitative and immunohistochemical analyses of BDNF in the rat retina. *Invest Ophthalmol Vis Sci* 44, 3211-3218.

Shi Z-H, Birman E, Saragovi H U (2007) Neurotrophic rationale in glaucoma: A TrkA agonist, but not NGF or a p75 antagonist, protects retinal ganglion cells in vivo. *Dev Neurobiol* 67, 884-94.

Surace E. M., Domenici L., Cortese K., Cotugno G., Di Vicino U., Venturi C., Cellerino A., Marigo V., Tacchetti, C. Ballabio A., Auricchio A. (2005). Rescue of functional and morphological abnormalities in the retina of the type I ocular albinism mouse model following adeno-associated viral mediated gene transfer. *Mol Ther* 12, 652-658.

Uccello-Barretta G, Nazzi S, Balzano F, Di Colo G, Zambito Y, Zaino C, Sansò M, Salvadori E, Benvenuti M. Enhanced affinity of ketotifen toward tamarind seed polysaccharide in comparison with hydroxyethylcellulose and hyaluronic acid: a nuclear magnetic resonance investigation. Bioorg Med Chem. 2008 Aug. 1; 16(15):7371-6.

Ventura L M, Porciatti V. Pattern electroretinogram in glaucoma. Curr Opin Ophthalmol. 2006 April; 17(2):196-202.

Watanabe W, Tokita Y, Kato M, Fukuda Y (2003) Intravitreal injections of neurotrophic factors and forskolin enhance survival and axonal regeneration of axotomized ganglion cells in cat retina *Neuroscience* 116, 733-742.

Yata T, Nakamura Ma Sagawa H, Tokita Y, H. Terasaki H, Watanabe M (2007) Survival and axonal regeneration of OFF-center retinal ganglion cells of adult cats are promoted with an anti-glaucoma drug, Nipradolol, but not BDNF and CNTF. *Neuroscience* 148, 53-64.

The invention claimed is:

1. A method of treating chronic simple glaucoma in a subject in need thereof comprising:
    administering an effective amount of an ophthalmic preparation in the form of eyedrops comprising Brain-Derived Neurotrophic Factor (BDNF) in a concentration from 15 to 200 µg/µl to said subject in need thereof, and
    treating said chronic simple glaucoma in said subject in need.

2. The ophthalmic preparation according to claim 1, comprising a saline solution as pharmaceutically acceptable carrier.

3. The ophthalmic preparation according to claim 2, wherein the saline solution contains 0.9% of sodium chloride.

4. The ophthalmic preparation according to claim 1, comprising a viscosified solution as further pharmaceutically acceptable carrier.

5. The ophthalmic preparation according to claim 4, wherein the viscosified solution is a solution comprising polysaccharide extracted from tamarind seeds (TSP).

6. The ophthalmic preparation according to claim 5, wherein TSP concentration ranges from 0.05 to 2% w/v.

7. The ophthalmic preparation according to claim 1, comprising hyaluronic acid.

8. The ophthalmic preparation according to claim 5, wherein the viscosified solution comprises TSP and hyaluronic acid.

* * * * *